United States Patent

Swiatek

Patent Number: 5,260,469
Date of Patent: Nov. 9, 1993

[54] ORGANO-SILOXANE WITH MODIFIED SOLUBILITY

[75] Inventor: Timothy P. Swiatek, Kenosha, Wis.

[73] Assignee: PPG Industries, Inc., Pittsburgh, Pa.

[21] Appl. No.: 857,863

[22] Filed: Mar. 26, 1992

[51] Int. Cl.$^5$ ............................................. C07F 7/08
[52] U.S. Cl. .................................................. 556/445
[58] Field of Search ..................................... 556/445

[56] References Cited

U.S. PATENT DOCUMENTS

| | | | |
|---|---|---|---|
| 3,122,899 | 3/1965 | Bailey | 556/445 |
| 3,280,160 | 10/1966 | Bailey | 556/445 X |
| 3,398,104 | 8/1968 | Haluska | 556/445 X |
| 3,402,192 | 9/1968 | Haluska | 556/445 X |
| 3,723,491 | 3/1973 | Rossny et al. | 556/445 X |
| 3,846,462 | 11/1974 | Prohai et al. | 556/445 X |
| 3,867,420 | 2/1975 | Morehouse et al. | 556/445 X |
| 4,740,496 | 4/1988 | Vanier | 503/227 |
| 4,797,501 | 1/1989 | Myerly et al. | 556/445 |
| 4,960,845 | 10/1990 | O'Lenick, Jr. | 528/25 |

*Primary Examiner*—Paul F. Shaver
*Attorney, Agent, or Firm*—George D. Morris

[57] ABSTRACT

Siloxane compounds represented by the formula:

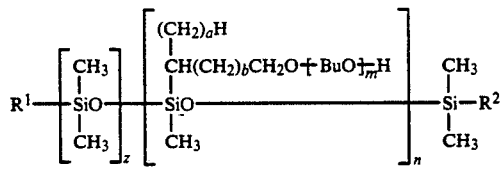

wherein:
(a) each BuO group in the molecule is independently a bivalent aliphatic —$C_4H_8$—O— group;
(b) $R^1$ and $R^2$ are each independently alkyl containing from 1 to about 18 carbon atoms, phenyl, 1-phenylethyl, 2-phenylethyl, 2-phenylpropyl, or 1-methyl-1-phenylethyl;
(c) the average value of m is in the range of from 2 to about 6;
(d) the value of n is an integer in the range of from 1 to about 6;
(e) the value of z is an integer in the range of from 1 to about 6;
(f) the average value of a is in the range of from 0 to 1;
(g) the average value of b is in the range of from 0 to 1; and
(h) the sum of the average values of a and b is 1;

are useful as components of cosmetics.

24 Claims, No Drawings

ORGANO-SILOXANE WITH MODIFIED SOLUBILITY

The present invention is directed to a siloxane which is especially useful as component in cosmetics, especially hair and skin preparations.

Accordingly, one embodiment of the invention is a siloxane compound represented by the formula:

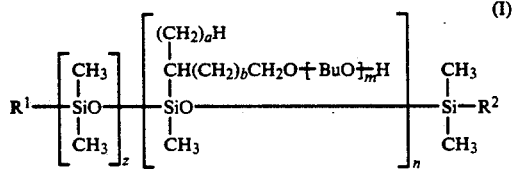

wherein: (a) each BuO group in the molecule is independently a bivalent aliphatic —$C_4H_8$—O— group; (b) $R^1$ and $R^2$ are each independently alkyl containing from 1 to about 18 carbon atoms, phenyl, 1-phenylethyl, 2-phenylethyl, 2-phenylpropyl, or 1-methyl-1-phenylethyl; (c) the average value of m is in the range of from 2 to about 6; (d) the value of n is 1 or 2; (e) the value of z is an integer in the range of from 1 to about 6; (f) the average value of a is in the range of from 0 to 1; (g) the average value of b is in the range of from 0 to 1; and (h) the sum of the average values of a and b is 1.

Another embodiment of the invention is a mixture of siloxane compounds, which mixture is represented by Formula (I) wherein: (a) each BuO group of each siloxane compound constituting the mixture is independently a bivalent aliphatic —$C_4H_8$—O— group; (b) $R^1$ and $R^2$ of each siloxane compound constituting the mixture are each independently alkyl containing from 1 to about 18 carbon atoms, phenyl, 1-phenylethyl, 2-phenylethyl, 2-phenylpropyl, or 1-methyl-1-phenylethyl; (c) the average value of m is in the range of from 2 to about 6; (d) the average value of n is in the range of from 1 to 2; (e) the average value of z is in the range of from 1 to about 6; (f) the average value of a is in the range of from 0 to 1; (g) the average value of b is in the range of from 0 to 1; and (h) the sum of the average values of a and b is 1.

Formula (I) is diagrammatic, and it is not intended to imply that the parenthetical portions subscripted by n and z are necessarily blocks, although blocks may be used where desired. In many cases the compound is more or less random, especially when more than a few siloxane units are employed and when mixtures are used. In those instances where more than a few siloxane units are used and it is desired to form blocks, oligomers are first formed and then these are joined to form the block compound. By the judicious choice of reactants, compounds having an alternating structure or blocks of alternating structure may be used.

The siloxane or mixture of siloxanes represented by FIG. (I) ordinarily has a high refractive index, usually at least about 1.44 at 25° C. and a wavelength of 589.3 nanometers. In most cases the refractive index under the same conditions is in the range of from about 1.44 to about 1.48. Such high refractive indices are beneficial in imparting an appearance of high gloss to the hair or skin to which cosmetic containing the siloxane or mixture of siloxanes has been applied.

The siloxane or mixture of siloxanes is usually characterized by its ability to impart lubricity to cosmetics, but without a tactually feeling of greasiness. This characteristic is especially beneficial in hair treatment preparations since it promotes detangling and the ability to be combed.

When the value of a for any individual —[BuO]$_m$H-functional siloxane unit is 1, the value of b for such unit will be 0. Likewise, when the value of a for the unit is 0, the value of b for the unit will be unity. For compounds or mixtures of compounds of the invention, the average values of a and b may be whole or fractional numbers such that a+b=1. It is preferred that the average value of a be about 0 and the average value of b be about 1. When the siloxane is prepared by reacting methylhydroxiloxane functionality with allyl functionality, the values of a and b will be determined by the distribution resulting from the manner in which the addition reaction occurs. For most purposes it is not necessary to analyze these compounds or mixtures of compounds for the average values of a and b, it being satisfactory to utilize the mixture as formed by the reaction. Nevertheless, it is permissible, and sometimes desirable, to modify the average values of a and b by adding appropriate amounts of specific compounds within Formula (I).

The bivalent aliphatic —$C_4H_8$—O— groups constituting the BuO groups of the molecule may be the same, they may be different, or some may be the same but different from one or more of the others. When the siloxane is prepared by reacting methylhydosiloxane functionality with the adduct of allyl alcohol and butylene oxide, the identities of the individual —$C_4H_8$—O— groups will be determined by factors such as: (a) whether 1,2-butylene oxide, 2,3-butylene oxide, or a mixture of both butylene oxide isomers is used in forming the adduct, (b) in the case of using a mixture of butylene oxide isomers, their relative proportions, and (c) in the case of 1,2-butylene oxide, the manner(s) in which the epoxide rings open. For most purposes it is not necessary to analyze the compounds and mixtures of the invention for the identities and proportions of the individual —$C_4H_8$—O— groups, it being satisfactory to utilize the mixture as formed by the reaction. The preferred —$C_4H_8$—O— group is the —$CH_2CH(CH_2CH_3)$—O— group.

The value of m for any individual —[BuO]$_m$H-functional siloxane unit will be an integer. For compounds or mixtures of compounds of the invention, the average value of m may be a whole or fractional number. When the siloxane is prepared by reacting methylhydrosiloxane functionality with an adduct of allyl alcohol and butylene oxide, the average value of m for the siloxane will be determined by the number of butylene oxide units which added to the allyl alcohol during preparation of the adduct. The average value of m for the compounds and mixture of the invention is in the range of from 2 to about 6. In many instances the average value of m is in the range of from about 3 to about 5. An average value of about 4 is preferred. The values of m for individual —[BuO]$_m$H-functional siloxane units may be 0, 1, 2, 3, 4, 5, 6, or even higher.

The values of n and z for any particular siloxane compound will be positive integers, while the average values of n and z for a mixture of compounds constituting the siloxane may independently be positive integers or positive numbers which are not integers.

The value of n for individual compounds of the invention may be 1 or 2. It is preferred that the value of n be 1. The average value of n for the mixture of the invention is in the range of from 1 to 2. An average value of about 1 is preferred. In the case of a mixture, the values of n for individual compounds constituting the mixture may be 0, 1, 2, 3, 4, 5, 6, or even higher.

The value of z for individual compounds of the invention may be an integer in the range of from 1 to about 6. Generally the value of z is an integer in the range of from 1 to about 4. Frequently the value of z is 1 or 2. It is preferred that the value of z be 1. The average value of z for the mixture of the invention is in the range of from 1 to about 6. In many instances the average value of z is in the range of from 1 to about 4. Often the average value of z is in the range of from 1 to about 2. An average value of about 1 is preferred. In the case of a mixture, the values of z for individual compounds constituting the mixture may be 1, 2, 3, 4, 5, 6, or even higher.

The values or average values of n and z may be ascertained from analytical information, knowledge of the structures of the reactants, knowledge of the proportions of reactants, knowledge of the reaction mechanism, knowledge of the reaction procedure, or various combinations of these. When an average molecular weight of a mixture of compounds is used in the determination, the number average molecular weight should be employed. The number average molecular weight may be found experimentally or it may be calculated from the distribution of individual compounds using the equalities:

$$\overline{M}_n = \frac{\Sigma M_k N_k}{\Sigma N_k} = \frac{\Sigma w_k}{\Sigma m_k}$$

where $\overline{M}_n$ is the number average molecular weight;
$M_k$ is the molecular weight of molecules of species k;
$N_k$ is the number of molecules of species k;
$w_k$ is the mass, expressed in grams, of molecules of species k; and
$m_k$ is the mass, expressed in gram-moles, of molecules of species k.

$R^1$ and $R^2$ of the siloxane compound of the invention are each independently alkyl containing from 1 to about 18 carbon atoms, phenyl, 1-phenylethyl, 2-phenylethyl, 2-phenylpropyl, or 1-methyl-1-phenylethyl. Often the alkyl contains from 1 to about 10 carbon atoms. In many cases the alkyl contains from 1 to about 4 carbon atoms. Methyl is preferred. Although $R^1$ and $R^2$ may be the same or different, it is preferred that they both be the same. It is particularly preferred that $R^1$ and $R^2$ are both methyl.

$R^1$ and $R^2$ of each siloxane compound constituting the mixture of the invention are each independently alkyl containing from 1 to about 18 carbon atoms, phenyl, 1-phenylethyl, 2-phenylethyl, 2-phenylpropyl, or 1-methyl-1-phenylethyl. Often the alkyl contains from 1 to about 10 carbon atoms. In many cases the alkyl contains from 1 to about 4 carbon atoms. Methyl is preferred. Although $R^1$ and $R^2$ may be the same or different, it is preferred that they both be the same. It is particularly preferred that $R^1$ and $R^2$ are both methyl.

The mixture of the invention may optionally comprise materials other than the siloxane compounds discussed above. Nevertheless, average values of a, b, m, n, and z for the mixture are determined only in respect of those compounds having the structure of Formula (I) in which the values of a, b, m, n, and z for compounds constituting the mixture are as discussed above.

The compounds and mixtures of the invention may be prepared by reacting $R^1,R^2$-terminated, methyl-functional, hydro-functional polysiloxane with the adduct of allyl alcohol and butylene oxide.

The bis(trimethyl)-terminated, methyl-functional, hydro-functional polysiloxanes are well known materials and are exemplified by:

1,1,1,3,5,5,5-Heptamethyltrisiloxane [CAS 1873-88-7]
1,1,1,3,5,7,7,7-Octamethyltetrasiloxane [CAS 16066-09-4]
1,1,1,3,3,5,7,7,7-Nonamethyltetrasiloxane [CAS 77606-50-9]

These compounds may be used as reactants with the adduct of allyl alcohol and butylene oxide when $R^1$ and $R^2$ are both methyl.

The series of known bis(trimethyl)-terminated, methyl-functional, hydro-functional polysiloxane compounds does not end with the tetrasiloxane, but continues to very high molecular weights. Such polysiloxanes containing 20, 30, 40, and 50 methylhydrosiloxane units, and even more, are known. Examples of these polymers include:

α-(Trimethylsilyl)-ω-((trimethylsilyl)oxy)-poly(oxy(methylsilylene)) [CAS 26403-67-8]
Poly(oxy(methylsilylene)) [CAS 9004-73-3]

The higher molecular weight $R^1,R^2$-terminated, methyl-functional, hydro-functional polysiloxanes are useful for preparing $R^1,R^2$-terminated, methyl-functional, hydro-functional polysiloxanes of lower molecular weight. This may be accomplished by equilibration of the higher molecular weight polysiloxanes with a simple disiloxane or a simple cyclotetrasiloxane in the presence of an acid catalyst. For example, the reaction represented diagrammatically and in unbalanced form:

(CH₃)₃SiO[(CH₃)(H)SiO]₃₀₋₅₀Si(CH₃)₃ + R¹(CH₃)₂SiOSi(CH₃)₂R² → R¹(CH₃)₂SiO[(CH₃)(H)SiO]₁₋₆Si(CH₃)₂R² may be conducted by recycling the reactants through a bed of acidic sulfonated polystyrene ion exchange resin beads (e.g., Amberlyst ® A-15 resin; Rohm & Haas Company) at about 60° C. for about 24 hours, or by stirring the reactants and about ½ percent by weight, based on the reactants, of trifluromethanesulfonic acid at about 60° C. for about 24 hours.

Examples of simple disiloxanes that may be used in the above equilibration reaction include:
Hexamethyldisiloxane [CAS 107-46-0]
1,1,3,3-tetramethyl-1,3-diphenyldisiloxane [CAS 56-33-7]

An example of a simple cyclotetrasiloxane that may be used in the equilibration reaction is:
octamethylcyclotetrasiloxane [CAS 556-67-2]

Simple disiloxanes where $R^1$ and $R^2$ are alkyl containing from 2 to about 18 carbon atoms, 1-phenylethyl, 2-phenylethyl, 2-phenylpropyl, or 1-methyl-1-phenylethyl, may be formed by reacting 1,1,3,3-tetramethyldisiloxane [CAS 3277-26-7] with the corresponding 1-alkene, styrene, or α-methylstyrene. The reaction is ordinarily conducted in the liquid phase and in the presence of a catalyst such as chloroplatinic acid. Usually the reaction is conducted at temperatures in the range of from about 20° C. to about 250° C. From about 80° C. to about 140° C. is preferred. Although superatmospheric or subatmospheric pressures may be used, the reaction is most often conducted at about ambient atmospheric pressure.

The adduct of allyl alcohol and butylene oxide may be prepared by reacting allyl alcohol with one or both of the butylene oxide isomers. The reaction is ordinarily conducted in the liquid phase in the presence of alkali metal hydroxide or alkaline earth metal hydroxide. The preferred alkali metal hydroxides are sodium hydroxide and potassium hydroxide. Potassium hydroxide is especially preferred. The reaction is usually conducted in the presence of about 0.15 percent by weight potassium hydroxide based on the total reactor charge. Any of the other hydroxides may be substituted for potassium hydroxide on an equivalent-for-equivalent basis. In most instances the reaction is conducted at temperatures in the range of from about 80° C. to about 200° C. From about 125° C. to about 135° C. is preferred. Although ambient or subatmospheric pressures may be used, the reaction is ordinarily conducted at superatmospheric pressures, preferably in the range of from about 34 to about 550 kilopascals, gauge. It is further preferred that the reaction be conducted under nitrogen or other inert gas.

The reaction of $R^1,R^2$-terminated, methyl-functional, hydro-functional polysiloxane with the adduct of allyl alcohol and butylene oxide is ordinarily conducted in the liquid phase and in the presence of a catalyst such as chloroplatinic acid. Usually the reaction is conducted at temperatures in the range of from about 20° C. to about 250° C. From about 80° C. to about 140° C. is preferred. Although superatmospheric or subatmospheric pressures may be used, the reaction is most often conducted at about ambient atmospheric pressure under an inert atmosphere.

The values or average values of n and z for the product are usually about the same as those of the $R^1,R^2$-terminated, methyl-functional, hydro-functional polysiloxane reactant.

The amount of the compound and/or mixture of the present invention used in cosmetics may be widely varied, depending upon many factors such as the identity of the compound and/or mixture, the identities and amounts of other components, the type of cosmetic, and the effect desired. In most cases, however, the compound and/or mixture of the invention constitutes from about 0.1 to about 10 percent by weight of the cosmetic. From about 2 to about 5 percent by weight is preferred.

The invention is further described in conjunction with the following example which is to be considered illustrative rather than limiting, and in which all parts are parts by weight and all percentages are percentages by weight unless otherwise specified.

EXAMPLE

To a 2-liter flask equipped with a mechanical stirrer, reflux condenser, and nitrogen inlet, were added 585 grams of the adduct of allyl alcohol and 1,2-butylene oxide at a molar ratio of 1:4 and 415 grams of 1,1,1,3,5,5,5-heptamethyltrisiloxane. The solution was heated with stirring to 100° C. and then 143 microliters of a catalyst solution containing 5 parts chloroplatinic acid, 10 parts acetic acid, and 85 parts isopropyl alcohol, by weight, was added to the mixture. The solution was then heated to 168° C. The solution was then cooled to 145° C. and held at that temperature for 2 hours. The solution was next heated to 170° C. and stripped under vacuum with a nitrogen sparge for 2 hours. The residue was cooled to 80° C. and 0.3 gram of a 50% aqueous hydrogen peroxide solution was added. The solution was heated to 145° C. and held at that temperature for one hour under an absolute pressure of 400 pascals. The solution was then cooled to 80° C. and 7 grams of magnesium silicate and 3 grams of water were added. The solution was stirred for one hour, cooled, and filtered. The resulting product was a light yellow, clear solution having a kinematic viscosity of 33.2 centistokes at 25° C. and a refractive index of 1.4356 at 25° C. and a wavelength of 589.3 nanometers. The Gardner Color of the product was 1-.

Although the present invention has been described with reference to specific details of certain embodiments thereof, it is not intended that such details should be regarded as limitations upon the scope of the invention except insofar as they are included in the accompanying claims.

I claim:

1. A siloxane compound represented by the formula:

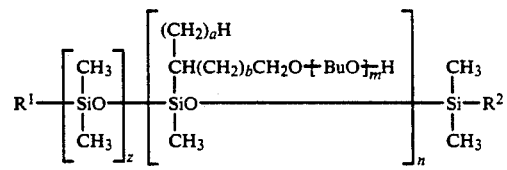

wherein:
(a) each BuO group in the molecule is independently a bivalent aliphatic —$C_4H_8$—O— group;
(b) $R^1$ and $R^2$ are each independently alkyl containing from 1 to about 18 carbon atoms, phenyl, 1-phenylethyl, 2-phenylethyl, 2-phenylpropyl, or 1-methyl-1-phenylethyl;
(c) the average value of m is in the range of from 2 to about 6;
(d) the value of n is 1 or 2;
(e) the value of z is an integer in the range of from 1 to about 6;
(f) the average value of a is in the range of from 0 to 1;
(g) the average value of b is in the range of from 0 to 1; and
(h) the sum of the average values of a and b is 1.

2. The siloxane compound of claim 1 wherein $R^1$ and $R^2$ are both methyl.

3. The siloxane compound of claim 1 wherein the average value of a is about 0 and the average value of b is about 1.

4. The siloxane compound of claim 1 wherein the value of z is an integer in the range of from 1 to about 4.

5. The siloxane compound of claim 1 wherein the value of n is 1 or 2 and the value of z is 1 or 2.

6. The siloxane compound of claim 1 wherein the value of n is 1 and the value of z is 1.

7. The siloxane compound of claim 1 wherein the average value of m is in the range of from about 3 to about 5.

8. The siloxane compound of claim 1 wherein the average value of m is about 4.

9. The siloxane compound of claim 2 wherein the average value of m is in the range of from about 3 to about 5, and the value of z is an integer in the range of from 1 to about 4.

10. The siloxane compound of claim 2 wherein the average value of m is about 4, the value of n is 1, and the value of z is 1.

11. The siloxane compound of claim 10 wherein the average value of a is about 0 and the average value of b is about 1.

12. The siloxane compound of claim 11 wherein each of said bivalent aliphatic —C$_4$H$_8$—O— groups is a —CH$_2$CH(CH$_2$CH$_3$)—O— group.

13. A mixture of siloxane compounds, which mixture is represented by the formula:

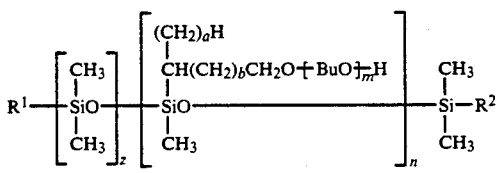

wherein:
(a) each BuO group of each siloxane compound constituting the mixture is independently a bivalent aliphatic —C$_4$H$_8$—O— group;
(b) R$^1$ and R$^2$ of each siloxane compound constituting the mixture are each independently alkyl containing from 1 to about 18 carbon atoms, phenyl, 1-phenylethyl, 2-phenylethyl, 2-phenylpropyl, or 1-methyl-1-phenylethyl;
(c) the average value of m is in the range of from 2 to about 6;
(d) the average value of n is in the range of from 1 to 2;
(e) the average value of z is in the range of from 1 to about 6;
(f) the average value of a is in the range of from 0 to 1;
(g) the average value of b is in the range of from 0 to 1; and
(h) the sum of the average values of a and b is 1.

14. The mixture of claim 13 wherein R$^1$ and R$^2$ are both methyl.

15. The mixture of claim 13 wherein the average value of a is about 0 and the average value of b is about 1.

16. The mixture of claim 13 wherein the average value of z is in the range of from 1 to about 4.

17. The mixture of claim 13 wherein the average value of z is in the range of from 1 to about 2.

18. The mixture of claim 13 wherein the average value of n is about 1 and the average value of z is about 1.

19. The mixture of claim 13 wherein the average value of m is in the range of from about 3 to about 5.

20. The mixture of claim 13 wherein the average value of m is about 4.

21. The mixture of claim 14 wherein the average value of m is in the range of from about 3 to about 5, and the average value of z is in the range of from 1 to about 4.

22. The mixture of claim 14 wherein the average value of m is about 4, the average value of n is about 1, and the average value of z is about 1.

23. The mixture of claim 22 wherein the average value of a is about 0 and the average value of b is about 1.

24. The mixture of claim 23 wherein each of said bivalent aliphatic —C$_4$H$_8$—O— groups is a —CH$_2$CH(CH$_2$CH$_3$)—O— group.

* * * * *